United States Patent
Gherlone

(10) Patent No.: US 10,143,540 B2
(45) Date of Patent: Dec. 4, 2018

(54) DENTAL IMPLANT SYSTEM

(71) Applicant: Enrico Gherlone, Due Carrare (PD) (IT)

(72) Inventor: Enrico Gherlone, Due Carrare (PD) (IT)

(*) Notice: Subject to any disclaimer, the term of this patent is extended or adjusted under 35 U.S.C. 154(b) by 2 days.

(21) Appl. No.: 15/279,253

(22) Filed: Sep. 28, 2016

(65) Prior Publication Data
US 2017/0258559 A1    Sep. 14, 2017

(30) Foreign Application Priority Data

Mar. 14, 2016   (IT) .................. 102016000026576

(51) Int. Cl.
*A61C 8/00*    (2006.01)

(52) U.S. Cl.
CPC .......... *A61C 8/0068* (2013.01); *A61C 8/0022* (2013.01); *A61C 8/0069* (2013.01); *A61C 8/0078* (2013.01)

(58) Field of Classification Search
CPC .... A61C 8/0068; A61C 8/0022; A61C 8/0069
See application file for complete search history.

(56) References Cited

U.S. PATENT DOCUMENTS

| | | | | |
|---|---|---|---|---|
| 5,040,982 A * | 8/1991 | Stefan-Dogar | ........ | A61C 8/005 433/169 |
| 6,709,270 B2 * | 3/2004 | Honkura | .............. | A61C 8/0018 433/174 |
| 8,951,042 B2 * | 2/2015 | Buchegger | ........... | A61C 8/0068 433/173 |
| 9,737,380 B2 * | 8/2017 | Hogan | ................. | A61C 8/0062 |
| 2003/0235802 A1 * | 12/2003 | Martina | ............... | A61C 8/0022 433/174 |
| 2005/0287497 A1 * | 12/2005 | Carter | .................... | A61C 8/005 433/173 |
| 2008/0261176 A1 * | 10/2008 | Hurson | ................ | A61C 8/0022 433/174 |
| 2013/0017513 A1 * | 1/2013 | Lutz | ....................... | A61C 8/005 433/174 |
| 2013/0295521 A1 * | 11/2013 | Olsson | ................. | A61C 8/0066 433/173 |
| 2014/0141387 A1 * | 5/2014 | Kikuchi | ............... | A61C 13/235 433/174 |
| 2014/0356813 A1 * | 12/2014 | Durr | .................... | A61C 8/0066 433/173 |
| 2015/0030993 A1 * | 1/2015 | von Malottki | ....... | A61C 8/0022 433/173 |
| 2016/0166358 A1 * | 6/2016 | Thome | ................. | A61C 8/0025 433/174 |

* cited by examiner

*Primary Examiner* — Nicholas Lucchesi
(74) *Attorney, Agent, or Firm* — Themis Law

(57) ABSTRACT

A dental implant system includes a dental implant, an abutment adapted to be inserted in an axial hole of the dental implant, and a locking screw adapted to be inserted in an axial through-hole of the abutment and to be screwed into the axial hole of the dental implant. The axial through-hole defined in the abutment includes a frustoconical portion configured to come into contact with a correspondingly frustoconical portion of the locking screw, wherein the median circumference of the frustoconical contact surface between the abutment and the tightening screw is configured to be disposed under the crest/connection line.

7 Claims, 3 Drawing Sheets

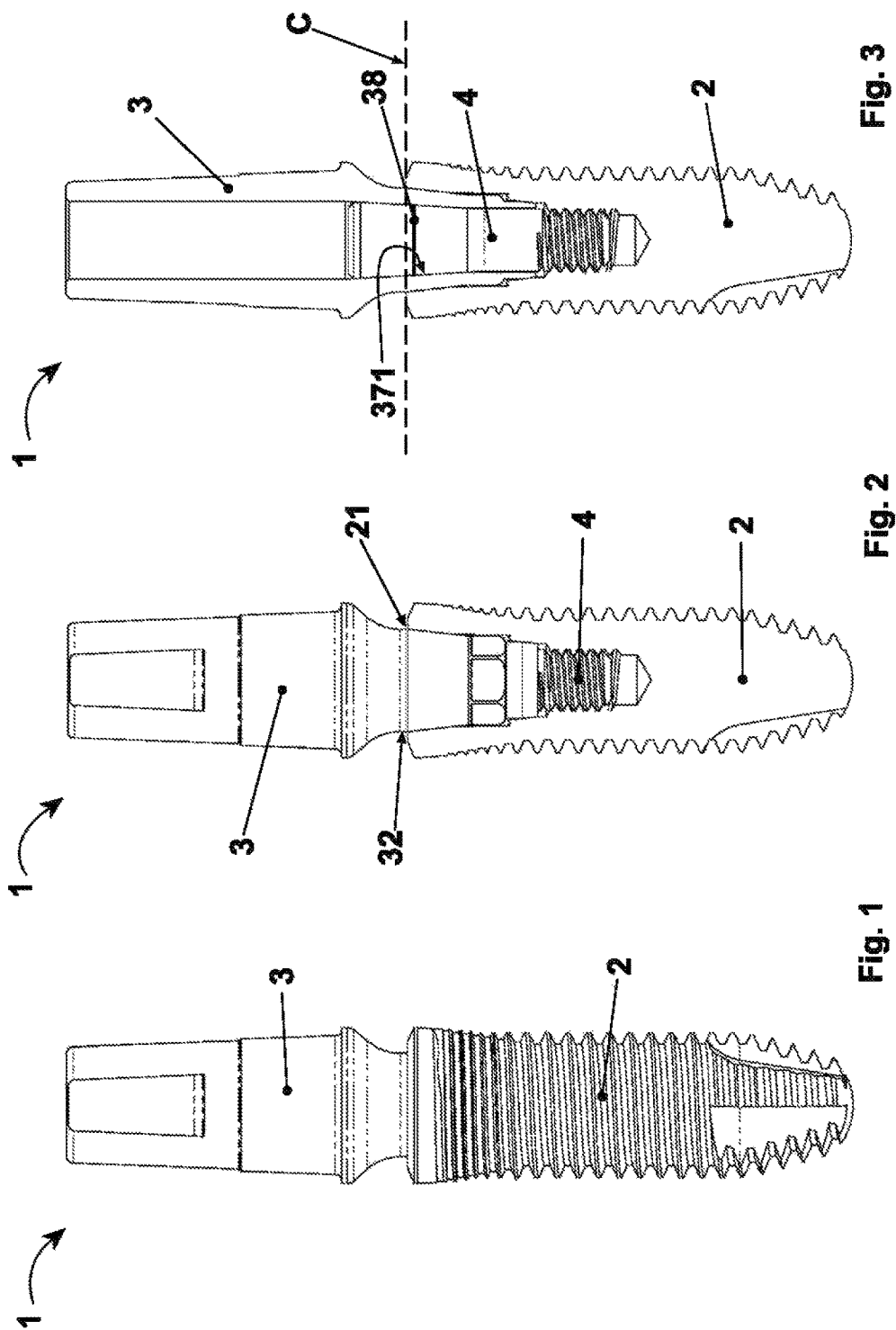

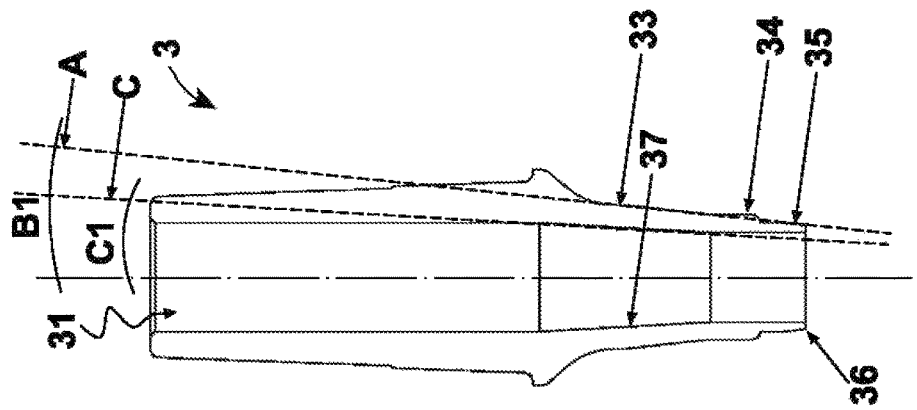
Fig. 7
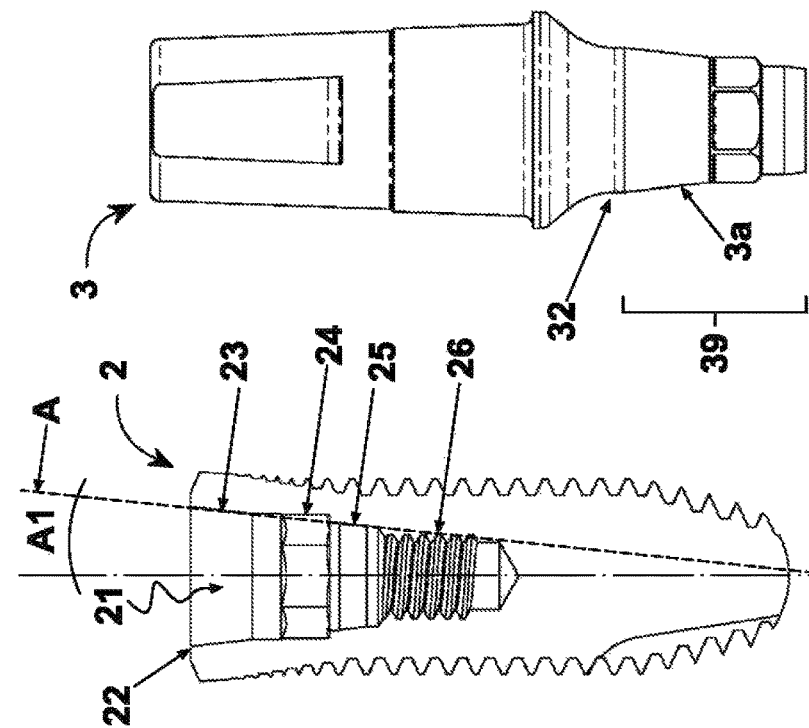
Fig. 6
Fig. 5
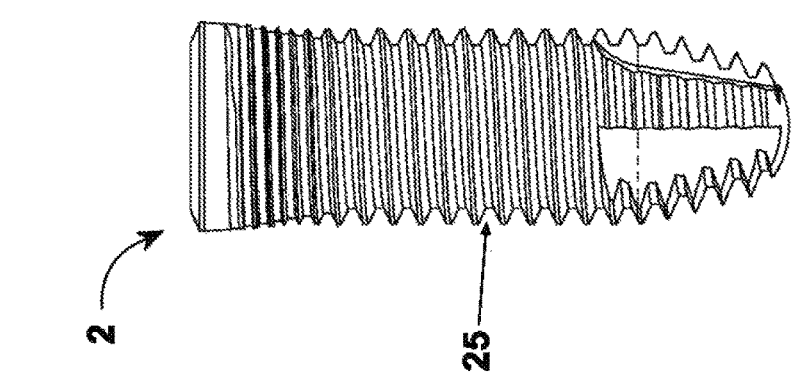
Fig. 4

DENTAL IMPLANT SYSTEM

FIELD OF THE INVENTION

The present invention relates to a dental prosthetic system. More particular, the present invention relates to a dental implant system.

BACKGROUND OF THE INVENTION

Dental implant systems are known, which include a dental implant, or a portion that is adapted to be inserted and bound to the jawbone; an abutment that is adapted to be inserted into the implant; a locking screw that is adapted to be screwed inside the implant and to lock the abutment to the implant; and a prosthesis that simulates a missing tooth and that is adapted to be bound to the abutment.

U.S. patent publication no. 2009/0239196 discloses a dental implant system comprising a dental implant, an abutment and a locking screw. The implant generally has a substantially cylindrical and elongated body, which is provided with an externally threaded portion for screwing into the jawbone of a patient, and with a blind inner hole configured for receiving the abutment and the locking screw.

The blind inner hole has, in descending order, a frustoconical first portion with an upperly widening portion, a cylindrical second portion, and a threaded third portion receiving the locking screw.

The abutment instead includes a substantially cylindrical elongated body, with an insertion portion adapted for inserting into the blind hole of the implant and with an outer surface conformed to mate with the surface of the blind inner hole of the implant. In particular, the insertion portion includes, in descending order, an upperly widening frustoconical first portion that mates with the frustoconical first portion of the blind inner hole of the implant, and a cylindrical second portion.

The abutment also has an axial through-hole for receiving the locking screw.

The locking screw includes an elongated cylindrical body configured for inserting in the through-hole of the abutment, and a threaded portion configured for screwing in the threaded third portion of the inner blind hole of the implant, causing the abutment to become coupled to the implant.

The axial hole of the abutment includes a frustoconical portion widening in an upper direction, which corresponds to a frustoconical portion of the head of the locking screw, where the inclination of the frustoconical portion is less than 15° from the longitudinal axis.

International publication no. WO 2006/128620 discloses a dental implant system that includes an abutment provided with guiding and locking means for joining the abutment to the dental implant.

In particular, the abutment includes a portion adapted for inserting into the blind hole of the implant and further includes, in descending order, a substantially frustoconical first portion that has a wider upper end, a second portion having anti-rotational means, and a third portion that operates as a guide for inserting the abutment into the blind hole.

Further, the abutment has an axial opening for inserting the locking screw that couples the abutment to the implant.

Dental implant systems must bear significant loads, especially during mastication.

In the known systems, the frustoconical contact surface between the inside of the abutment and the locking screw is substantially level with, and for the most part above, the crest line in case of standard positioning.

More generally, in the event of an above crest or below crest positioning, the frustoconical surface becomes mostly positioned above the connecting circumference, corresponding to the real junction circumference among the different frustoconical surfaces.

For ease of discussion, reference will be made hereinafter to the crest/connection line, so as to include all possible situations.

In fact, the elevational midpoints of the contact frustoconical surface between the inside of the abutment and the locking screw defines a circumference, hereinafter called a median circumference. That medial circumference is substantially above the crest/connection line.

Consequently, all loads are unbalanced upwardly and frequently cause ruptures of parts of the implant system, for example, of the collar of the implant, where the majority of mastication loads are concentrated.

SUMMARY OF THE INVENTION

An improved dental system has been studied and developed that addresses the above described drawbacks.

A main objective of the present invention is to increase unscrewing torque, consequently increasing resistance to loads and reducing the risk of ruptures of parts of the implant system.

Another objective of the present invention is to increase joint strength among the different parts of the implant system.

These and other objectives, whether direct or complementary, are achieved by a dental implant system according to the invention that includes a dental implant, an abutment adapted for inserting in a blind axial hole provided in the dental implant, and a locking screw adapted for inserting in an axial through-hole defined in the abutment and for engaging the wall of the blind hole in the dental implant, so as to engage the abutment with the implant. The axial hole in the abutment includes a frustoconical portion that widens upwardly and contacts the locking screw, which is correspondingly wedge-shaped. The median circumference of the frustoconical portion, which provides contact between the abutment hole and the locking screw, is positioned substantially below the crest line.

As a consequence, by lowering the median circumference to below the crest/connection line, the initial unscrewing torque is increased and the unscrewing surface and force are maximized.

Preferably, the abutment has an outer surface that is frustoconical at least in part and that engages the blind hole in the implant with a different inclination, preferably a larger one, in comparison to the inclination of the frustoconical portion of the through-hole.

In another aspect, a dental implant system according to the invention has a blind hole in the implant that includes, in descending order, an upperly widening frustoconical first portion, a connecting second portion, an upperly widening frustoconical third portion, and a threaded fourth portion receiving the locking screw, wherein the two frustoconical portions have the same angle of inclination.

These two frustoconical portions are disposed on the same imaginary conical surface, providing for a continuous conicity, except for the connecting portion.

Likewise, the abutment includes an insertion portion, which is adapted for inserting into the blind hole of the implant and has a mating shape with the blind hole, and which is further shaped to mate with the blind hole and includes, in descending order, an upperly widening first frustoconical portion, a connecting second portion, and an upperly widening frustoconical third portion positioned adjacently to the extremity of the abutment. The two frustoconical portions have the same inclination and lie on the same imaginary conical surface.

This design substantially extends the length of the insertion portion and, therefore, the sealing surface of the abutment within the blind hole of the implant.

The angle of inclination of the frustoconical portions of the outer surface of the abutment is, in an axial direction, preferably larger that the angle of inclination of the frustoconical portion of the axial hole of the abutment.

Consequently, an implant-abutment-screw coupling is achieved on non-parallel planes, thereby reducing stress.

The wedge-shaped locking screw may include, in descending order, that is, starting from the head, an upperly widening frustoconical first portion that mates with the frustoconical portion of the through-hole of the abutment, and a threaded second portion that is adapted for screwing into the blind hole of the abutment.

In one embodiment, the frustoconical portion is subdivided in two frustoconical portions divided by a connecting portion, wherein the two frustoconical portions have frustoconical surfaces that preferably have the same inclination and lie on the same imaginary conical surface.

The upper frustoconical portion is configured to mate with the frustoconical portion of the abutment and, accordingly, becomes positioned substantially above the crest/connection line.

BRIEF DESCRIPTION OF THE DRAWINGS

Features of a dental implant system according to the invention will detailed in greater depth in the following description with reference to the enclosed drawing figures, which are intended to be exemplary and not limiting.

FIGS. 1, 2 and 3 depict respectively a side view of a dental implant system according to the invention, a cross-section of the implant only, and a cross-section, in which a wedge-shaped locking screw is shown.

FIGS. 4 and 5 depict a side view and a cross-section view of an implant according to the invention.

FIGS. 6 and 7 depict a side view and a cross-section view of an abutment according to the invention.

DETAILED DESCRIPTION OF EMBODIMENTS OF THE INVENTION

Figure 9:
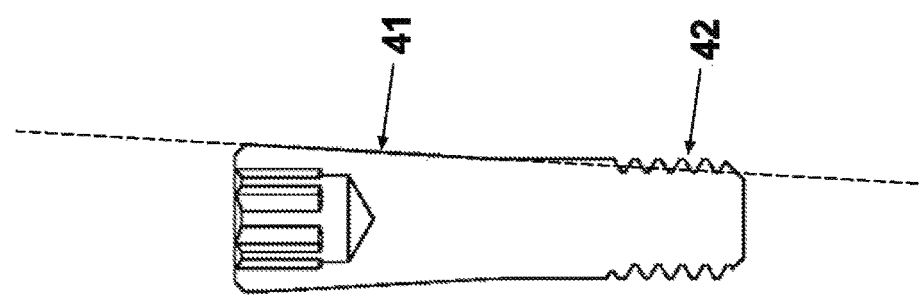
FIGS. 8 and 9 depict a side view and a cross-section view of a locking screw according to the invention.
Figure 8:
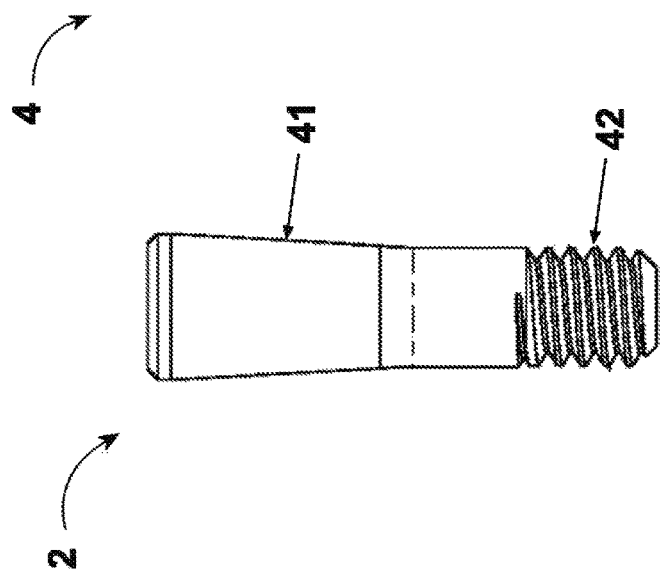

A dental implant system 1 according to the invention includes a dental implant 2 configured for engaging in the jawbone of a patient, an abutment 3 configured for inserting in an axial hole 21 of the dental implant 2, and a locking screw 4 configured for inserting into an axial through-hole 31 of the abutment 3 and for screwing in the axial hole 21 of the dental implant 2, so as to achieve a coupling of the abutment 3 with the dental implant 2.

The implant 2 includes an outer portion 25 that is threaded and is adapted for screwing into the jawbone of the patient, and an axial hole 21 that receives the abutment 3.

The axial hole 21 of the dental implant 2 includes, in descending order, that is, from the opening 22 of abutment insertion, an upperly widening frustoconical first portion 23, a connecting second portion 24, an upperly widening frustoconical third portion 25, and a threaded fourth portion 26, into which the locking screw 4 is engaged.

The two frustoconical portions 23 and 25 of the implant 2 preferably have the same angle of inclination A1 and preferably lie on the same imaginary conical surface A, providing for a continuous conicity except for the connecting second portion 24.

The abutment 3 includes, in turn, an elongated body having an insertion portion 39, which is configured for inserting into the blind hole 21 of the implant 2 and has a shape that mates with the blind hole 21. The elongated body of the abutment 3 further defines the blind through-hole 31.

The insertion portion 39 includes, on its outer surface 3a, starting from the area 32 that mates with the opening 22 in the blind hole 21 of the implant 2, an upperly widening frustoconical first portion 33, a connecting second portion 34, and an upperly widening frustoconical third portion 35 that is adjacent to the lower end 36 of the abutment 3.

In one embodiment, the two frustoconical portions 33 and 35 have the same angle of inclination B1 and preferably define a single, continuous imaginary conical surface B except for the same connecting portion 34.

The angle of inclination B1 of the frustoconical portions 33 and 35 of the outer surface 3a substantially corresponds to the angle of inclination A1 of the frustoconical portions 23 and 25 of the blind axial hole 21 of the implant 2.

The through-hole 31 of the abutment 3 includes a frustoconical portion 37 that is upperly wider and that is shaped to contact the correspondingly frustoconical first portion 41 of the locking screw 4, wherein the median circumference 38 of the frustoconical contact surface 371 between the abutment 3 and the locking screw 4 is substantially below the crest connection line C, as shown in FIG. 3 and as previously described.

In one embodiment, the angle of incidence B1 of the frustoconical portions 33 and 35 of the outer surface 3a of the abutment 3 is different, and in particular larger, than the angle of inclination C1 of the frustoconical portion 37 of the axial through-hole 31 of the abutment 3.

The locking screw 4 includes, in descending order, the frustoconical first portion 41 and the threaded portion 42 configured to screw into the blind hole 21 of the implant 2.

In one embodiment, not shown in the figures, the locking screw 4 includes also a connecting second portion adjacent to the frustoconical first portion 41, and a frustoconical third portion, which has a surface with the same inclination and lies on the same conical surface as the first frustoconical portion 41.

While the invention has been described in connection with the above described embodiments, it is not intended to limit the scope of the invention to the particular forms set forth, but on the contrary, it is intended to cover such alternatives, modifications, and equivalents as may be included within the scope of the invention. Further, the scope of the present invention fully encompasses other embodiments that may become obvious to those skilled in the art and the scope of the present invention is limited only by the appended claims.

Therefore, with reference to the preceding description and the enclosed drawings, the following claims are set forth.

The invention claimed is:

1. A dental implant system comprising:
a dental implant adapted to be constrained to a patient's jawbone;
an abutment adapted to be inserted in an axial hole defined in said dental implant; and
a locking screw adapted to be inserted into an axial through-hole defined in said abutment and to be screwed in said axial hole defined in said dental implant so as to obtain a coupling between said abutment and said dental implant, wherein said axial through-hole defined in said abutment comprises an upwardly widening frustoconical portion, shaped to come into contact with a first mating frustoconical portion of said locking screw, wherein a middle circumference of a frustoconical contact surface between said abutment and said locking screw is adapted to be disposed substantially below a crest/connection line of the patient, wherein said abutment comprises an external surface that has at least partially a frustoconical shape and is adapted to be fitted in said axial hole defined in said implant, said external surface having an angle of inclination that is different from an angle of inclination of said frustoconical portion of said axial through-hole, and wherein said axial hole defined in said dental implant is blind and comprises, in descending order from an opening where the abutment is introduced, an upperly widening frustoconical first portion, a connecting second portion, an upperly widening frustoconical third portion, and a threaded fourth portion shaped to receive said locking screw, and wherein said frustoconical first and third portions have a same angle of inclination.

2. The dental implant system according to claim 1, wherein said frustoconical first and third portions lie on a same imaginary conical surface, thus defining a continuous conical surface except for said connecting second portion.

3. The dental implant system according to claim 1,
wherein said abutment comprises an insertion portion configured to be inserted into said axial hole of the dental implant and having a shape that matches a shape of said axial hole, wherein said insertion portion in turn comprises externally, in descending order starting from a side configured to coincide with said opening of said hole defined in the dental implant, an upperly widening frustoconical first portion, a connecting second portion, and an upperly widening frustoconical third portion, said third portion of said insertion portion being in proximity to an end of said abutment, and wherein said frustoconical first and third portions have a same angle of inclination.

4. The dental implant system according to claim 3, wherein said frustoconical first and third portions of said insertion portion define a single and continuous imaginary conical surface except for said connecting second portion of said insertion portion.

5. The dental implant system according to claim 3, wherein the angle of inclination of said frustoconical first and third portions of an external surface of said abutment is different from the angle of inclination of said frustoconical portion of said axial through-hole defined in the abutment.

6. The dental implant system according to claim 3, wherein the angle of inclination of said frustoconical first and third portions of an external surface of said abutment is larger than the angle of inclination of said frustoconical portion of said axial through-hole defined in the abutment.

7. The dental implant system according to claim 1, wherein said locking screw comprises, in descending order, said frustoconical first portion, a connecting second portion, a frustoconical third portion, and a threaded fourth portion adapted to be screwed into said blind hole defined in said dental implant, and wherein a surface of said frustoconical third portion of said locking screw has a same inclination and lies on a same imaginary conical surface as said frustoconical first portion of said locking screw.

* * * * *